United States Patent [19]

Robben et al.

[11] Patent Number: 5,803,130

[45] Date of Patent: Sep. 8, 1998

[54] MULTILAYER TUBE OR SHEET

[75] Inventors: Petrus A. M. Robben, Lelystad; Petrus J. A. Karsten, Enkhuizen; Martines W. Vonk, Abcoude, all of Netherlands

[73] Assignee: SOLVAY (Société Anonyme), Brussels, Belgium

[21] Appl. No.: 638,392

[22] Filed: Apr. 29, 1996

[30] Foreign Application Priority Data

May 12, 1995 [BE] Belgium .............................. 09500431

[51] Int. Cl.⁶ ..................................................... F16L 11/04
[52] U.S. Cl. ............................ 138/137; 138/140; 138/141
[58] Field of Search .................................... 138/137, 140, 138/141

[56] References Cited

U.S. PATENT DOCUMENTS

| | | | |
|---|---|---|---|
| 3,741,253 | 6/1973 | Brax et al. | 138/141 |
| 3,836,620 | 9/1974 | Bhuta et al. | |
| 4,101,699 | 7/1978 | Stine et al. | 138/141 |
| 4,482,587 | 11/1984 | Fagerburg et al. | 138/141 |
| 4,634,615 | 1/1987 | Versteegh et al. | 138/141 |
| 4,643,927 | 2/1987 | Luecke et al. | 138/141 |
| 5,171,640 | 12/1992 | Wirth. | |
| 5,469,892 | 11/1995 | Noone et al. | 138/122 |
| 5,474,109 | 12/1995 | Stoeppelmann et al. | 138/141 |
| 5,611,373 | 3/1997 | Ashcraft | 138/141 |

FOREIGN PATENT DOCUMENTS

| | | |
|---|---|---|
| 0160984 | 11/1985 | European Pat. Off. . |
| 0216639 | 4/1987 | European Pat. Off. . |
| 0326827 | 8/1989 | European Pat. Off. . |
| 0380270 | 8/1990 | European Pat. Off. . |
| 0389695 | 10/1990 | European Pat. Off. . |
| 0506348 | 9/1992 | European Pat. Off. . |
| 59-083651 | 5/1984 | Japan . |
| 05200951 | 8/1993 | Japan . |

*Primary Examiner*—Denise L. Ferensic
*Assistant Examiner*—James F. Hook
*Attorney, Agent, or Firm*—Spencer & Frank

[57] ABSTRACT

Multilayer tube or sheet including an intermediate layer, an inner layer bonded to the inner surface of the intermediate layer and an outer layer bonded to the outer surface of the intermediate layer, in which the intermediate layer comprises a polymeric material chosen from terpolymers of ethylene, of maleic anhydride and of an acrylate.

14 Claims, No Drawings

MULTILAYER TUBE OR SHEET

FIELD OF THE INVENTION

The present invention relates to a multilayer tube or sheet intended particularly for use in the medical field.

TECHNOLOGY REVIEW

Plastic sheets are commonly employed for the manufacture of pouches intended in particular for the packaging of liquids for medical use.

Plastic tubes are also commonly employed, especially as connections for the abovementioned pouches, for introducing or extracting material from these pouches, and as means for conveying liquids for medical use which are, for example, to be introduced into the human body for the purpose of therapy or analysis.

Plastics that can be employed for these applications must exhibit specific properties. In particular, they must be flexible and must offer sufficient mechanical strength. They must also be strictly compatible with the liquids and/or the constituent materials of the other components (pouches, accessories, etc.) with which they will be in contact. They must also withstand sterilization temperatures of the order of 120° C., at which the articles are usually treated, and must retain their properties after such a treatment.

Pouches for medical use are conventionally manufactured from sheets based on flexible vinyl chloride polymer (PVC), that is to say polymer to which at least one plasticizer has generally been added.

It is known today to manufacture these pouches alternatively from polyolefin-based sheets without addition of plasticizer. It is taught, in particular (EP 216639), to employ, for the packaging of physiological solutions, a multilayer sheet including a layer consisting of polyolefin or of polyester and another layer consisting of a mixture of polyolefin and of an elastomer.

Tubes made of suitable plastic must therefore be designed in order to meet, in particular, the above-mentioned requirement of compatibility with the novel constituent materials of the pouches and of the accessories with which they must be put together.

It is consequently known to manufacture, especially by coextrusion, multilayer tubes for medical use which can be fitted together with pouches or accessories in a simple and perfectly reliable manner, for example by welding (thermal, high frequency, etc.). In document EP 380270 a description is given of a three-layer tube for medical use, intended to be fitted together with a pouch or another package for medical use, including an intermediate layer including a polymeric material promoting flexibility, an inner layer bonded to the inner surface of the intermediate layer and including a heat-resistant material, and an outer layer bonded to the outer surface of the intermediate layer and including polypropylene, a copolymer of ethylene and of propylene or a modified copolymer of ethylene and of propylene. According to this document the polymeric material of the intermediate layer may in particular include polyethylene of very low density, a copolymer of ethylene and of vinyl acetate, a modified copolymer of ethylene and of vinyl acetate, a copolymer of ethylene and of methyl acrylate, a modified copolymer of ethylene and of methyl acrylate, a vinyl chloride polymer, a vinylidene chloride polymer, a mixture of a copolymer of ethylene and of vinyl acetate and of a modified copolymer of ethylene and of methyl acrylate, a mixture of polyethylene of very low density and of a modified copolymer of ethylene and of methyl acrylate, or a mixture of polyethylene of very low density and of a copolymer of ethylene and of vinyl acetate.

In addition to the abovementioned requirements the multilayer tubes for medical use must exhibit, in particular, a sufficient resistance to the delamination of their constituent layers, especially after the sterilizing heat treatment and after their fitting together with other components.

SUMMARY OF THE INVENTION

The first subject-matter of the present invention is therefore a multilayer tube intended especially for a medical use, satisfying the abovementioned requirements and offering, in particular, a very high resistance to the delamination of its constituent layers.

The invention relates more precisely to a multilayer tube including an intermediate layer, an inner layer bonded to the inner surface of the intermediate layer and an outer layer bonded to the outer layer of the intermediate layer, which is characterized in that the intermediate layer comprises a polymeric material chosen from the terpolymers of ethylene, of maleic anhydride and of an acrylate of formula $CH_2\!=\!CHCO_2R$ in which R is of formula $C_xH_{(2x+1)}$ with x=0, 1, 2 or 4, copolymers of ethylene and of ethyl acrylate, modified copolymers of ethylene and of ethyl acrylate and mixtures thereof.

DETAILED DESCRIPTION OF THE INVENTION

The multilayer tube includes an intermediate layer and at least two other layers, an inner layer and an outer layer. It may optionally include one or more other additional layers. The intermediate layer is preferably bonded directly to the inner layer and to the outer layer. Excellent results have been obtained with a tube consisting of the abovementioned three layers.

The intermediate layer comprises a polymeric material chosen from terpolymers of ethylene, of maleic anhydride and of an acrylate of formula $CH2\!=\!CHCO_2R$, in which R is of formula $C_xH_{(2x+1)}$ with x=0, 1, 2 or 4, copolymers of ethylene and of ethyl acrylate, modified copolymers of ethylene and of ethyl acrylate and mixtures thereof. It may also comprise other components, in particular other polymers. The usual additives, especially stabilizers, may also optionally be added. The intermediate layer preferably consists essentially of such a polymeric material.

The term modified is here intended to denote a copolymer or, more broadly, any polymer in which at least some constituent components have been replaced by others, with a view to substantially improving some of their properties. Such a modification may be carried out especially during the polymerization or after the latter, even during the mixing with a view to extrusion. A copolymer or a graft polymer may be mentioned in particular by way of example of a copolymer or of a modified polymer. Thus, copolymers or modified polymers are preferably modified by grafting of maleic anhydride.

Among the copolymers, the modified copolymers of ethylene and of ethyl acrylate have been found advantageous.

The intermediate layer preferably comprises a polymeric material chosen from the terpolymers of ethylene, of maleic anhydride and of an acrylate of formula $CH_2\!=\!CHCO_2R$ in which R is of formula $C_xH_{(2x+1)}$ with x=0, 1, 2 or 4, in particular with x=0, 1 or 2. Still more particularly the intermediate layer comprises a polymeric material chosen from terpolymers of ethylene, of maleic anhydride and of an acrylate of formula $CH_2\!=\!CHCO_2R$ in which R is of formula $C_xH_{(2x+1)}$ with x=1 or 2. A particularly advantageous multilayer tube has been obtained when the intermediate layer comprises a polymeric material chosen from the terpolymers of ethylene, of maleic anhydride and of an acrylate of formula $CH_2=CHCO_2R$ in which R is of formula $C_xH_{(2x+1)}$ with x=2. On the other hand, the terpolymers of ethylene, of maleic anhydride and of an acrylate of formula $CH_2=CHCO_2R$ in which R is of formula $C_xH_{(2x+1)}$ with x=3 have not been adopted as polymeric material for the intermediate layer, bearing in mind their toxicity with a view to the intended applications of the tubes in the medical field.

The relative thickness of the intermediate layer must be adapted to the materials used in the various layers and to the subsequent constraints on the use of the multilayer tube. The intermediate layer generally has a thickness corresponding to at least 1% of the total thickness of the tube wall. Its thickness preferably corresponds to at least 5% of the total thickness of the tube wall. Still more preferably, its thickness corresponds to at least 15% of the total thickness of the tube wall. The thickness of the intermediate layer in most cases does not exceed 99% of the total thickness of the tube wall. Advantageously this thickness corresponds to at most 50% of the total thickness of the tube wall. Still more advantageously, this thickness corresponds at most to 30% of the total thickness of the tube wall.

The materials used in the inner layer and/or in the outer layer must also be adapted to the materials of the other layer(s), to the processing constraints and to the subsequent constraints on the use of the multilayer tube. At least the inner layer or the outer layer preferably comprises a polymeric material chosen from polypropylene, modified polypropylenes, polyethylene, modified polyethylenes, copolymers of ethylene and of propylene, modified copolymers of ethylene and of propylene, copolymers of ethylene and of vinyl acetate, modified copolymers of ethylene and of vinyl acetate, styrene-ethylene-butylene-styrene block copolymers, modified styrene-ethylene-butylene-styrene block copolymers, polyurethanes, modified polyurethanes, polyether amide block copolymers, vinyl chloride polymers, modified vinyl chloride polymers, plasticized vinyl chloride polymers, modified and plasticized vinyl chloride polymers, polyamides, copolymers of ethylene and of an acrylic ester, polyesters, copolyesters and mixtures thereof.

According to a first method of use of the multilayer tube in the medical field, it may be fitted together via its external surface with a pouch for medical use in order to receive in its interior an accessory which is to be connected to the pouch.

According to a second method of use the multilayer tube may be fitted together via its external surface with an accessory and may convey in its interior a liquid for medical use.

It is necessary that the layer(s) which is(are) to be in contact with an accessory should comprise a polymeric material which is compatible with this accessory. In this case in particular, each layer involved, that is at least the inner layer or the outer layer, preferably comprises a polymeric material chosen from plasticized vinyl chloride polymers, polyurethanes, polyether amide block copolymers and mixtures of a copolymer of ethylene and of vinyl acetate with a copolyester. In a particularly preferred manner, each layer involved consists essentially of such a polymeric material.

It is also recommended that the layer(s) which is(are) to be in contact with a pouch or with a liquid for medical use should comprise a polymeric material which is compatible with the corresponding component. In this case, in particular, each layer involved, that is at least the inner layer or the outer layer, should advantageously comprise a polymeric material chosen from polypropylene, copolymers of ethylene and of propylene, modified copolymers of ethylene and of propylene, ternary mixtures of polypropylene or of a copolymer of ethylene and of propylene or of a modified copolymer of ethylene and of propylene with a copolymer of ethylene and of an acrylic ester and with a styrene-ethylene-butylene-styrene block copolymer. In a particularly advantageous manner each layer in question consists essentially of such a polymeric material.

In particular in the case of a multilayer tube intended for the first method of use as defined above it is advantageous to adopt the inner layer comprising a polymeric material chosen from plasticized vinyl chloride polymers, polyurethanes, polyether amide block copolymers or mixtures of a copolymer of ethylene and of vinyl acetate with a copolyester, and the outer layer including a polymeric material chosen from polypropylene, copolymers of ethylene and of propylene, modified copolymers of ethylene and of propylene, ternary mixtures of propylene or of a copolymer of ethylene and of propylene or of a modified copolymer of ethylene and of propylene with a copolymer of ethylene and of an acrylic ester and with a styrene-ethylene-butylene-styrene block copolymer. In a particularly advantageous manner the inner layer and the outer layer consist essentially of these polymeric materials.

In the case, in particular, of a tube intended for the second method of use as defined above, it is, on the contrary, advantageous to adopt the inner layer comprising a polymeric material chosen from polypropylene, copolymers of ethylene and of propylene, modified copolymers of ethylene and of propylene, ternary mixtures of polypropylene or of a copolymer of ethylene and of propylene or of a modified copolymer of ethylene and of propylene with a copolymer of ethylene and of an acrylic eater and with a styrene-ethylene-butylene-styrene block copolymer, and the outer layer including a polymeric material chosen from plasticized vinyl chloride polymers, polyurethanes, polyether amide block copolymers or mixtures of a copolymer of ethylene and of vinyl acetate with a copolyester. In a particularly advantageous manner the inner layer and the outer layer consist essentially of these polymeric materials.

The multilayer tube according to the invention is particularly adapted to use in the medical field, especially in that it satisfies the abovementioned requirements for this purpose and in that it offers a very high resistance to the delamination of its constituent layers, especially after the sterilizing heat treatment and after its optional fitting together with other components.

The present invention consequently also relates to the use in the medical field of the multilayer tube as defined above.

In view of the particularly advantageous properties of the multilayer structure of the tube defined above, this structure may also be advantageously adopted for a multilayer sheet.

The invention consequently also has as its subject-matter a multilayer sheet including layers such as defined above in the multilayer tube.

Finally, the invention relates to the use of this multilayer sheet in the medical field.

Finally, it will be noted that the properties of the multilayer tubes and sheets according to the invention may optionally be improved, in particular with a view to their sterilization, by subjecting these products to an irradiation treatment using an electron beam and/or electromagnetic radiation and/or by the incorporation of one or a number of conventional crosslinking agents such as, for example, peroxides.

EXAMPLES

Tubes with an external diameter of 8 mm, consisting of three layers of compositions as reproduced in the tables below were manufactured by coextrusion.

Examples 1R to 4R are given by way of comparison.

Examples 5 to 9 illustrate the invention without any limitation being implied.

The resistance to delamination of each tube was then measured, before and after a steam sterilization treatment at 121° C. lasting 30 minutes.

To measure this resistance to delamination a section approximately 10 cm in length was taken for each tube. Each tube section was cut into 2 or 3 pieces in the direction of the length. The two layers which had the lowest adhesion (according to all these examples, the plasticized PVC layer and the intermediate layer) were separated manually over a length of approximately 2 cm from one end of each piece. The partially separated layers were then placed in the jaws of a tensometer and each piece was delaminated at a constant speed of separation of the two parts of the jaw of 100 mm/min, the force required for this purpose being measured. The representative value of this force [N] was then recorded when it became constant, and was divided by the length [mm] of each test piece to obtain the resistance [N/mm] to delamination mentioned in the tables below.

TEHTM=tri(2-ethylhexyl) trimellitate
(1) parts by weight relative to 100 parts of PVC
(2) parts by weight relative to the composition
(3) Dainippon MK-2S composition
(4) Solvay Eltex® P KL 104
(5) Atochem Lotryl® 30BA02
(6) Mitsui Admer® NF530E
(7) Atochom Lotryl 3610
(8) Exxon Escorene® UL00328
(9) Atochem Lotader 4700

We claim:

1. A multilayer tube having a tube wall including an intermediate layer, an inner layer bonded to the inner surface of the intermediate layer and an outer layer bonded to the outer surface of the intermediate layer, in which the intermediate layer has a thickness from 15% to 50% of the total thickness of the tube wall, and comprises a polymeric material which is a terpolymer of ethylene, maleic anhydride and an acrylate of formula $CH_2=CHCO_2R$ in which R is of formula $C_xH_{(2x+1)}$ with x=1 or 2.

TABLE 1

| | Outer layer | | Intermediate layer | | Inner layer Plasticized PVC composition | | | Resistance to delamination | |
|---|---|---|---|---|---|---|---|---|---|
| Ex. | Composition | e [μm] | Composition | e [μm] | Plasticizer | Proportion (1) | e [μm] | Before sterilization [N/mm] | After sterilization [N/mm] |
| 1R | PP + EAE + SEBS (3) | 180 | EBA (5) | 150 | DEHP | 50 | 640 | 0.74 | 0.16 |
| 2R | PP + EAE + SEBS (3) | 150 | EVA mod | 150 | DEHP | 50 | 700 | 0.06 | 0.02 |
| 3R | PP + EAE + SEBS (3) | 130 | AM (6) | 170 | DEHP | 50 | 650 | 1.91 | 1.29 |
| 4R | PP + EAE + SEBS (3) | 140 | EMA (7) EVA (8) | 170 | DEHP | 50 | 660 | 1.52 | 1.22 |
| 5 | 85% (2) PP + EAE + SEBS (3) 15% EPC (4) | 100 | terpolymer E + EA + AM (9) | 200 | DEHP | 50 | 640 | 2.18 | 2.38 |
| 6 | 85% (2) PP + EAE + SEBS (3) 15% EPC (4) | 160 | terpolymer E + EA + AM (9) | 200 | TEHTM | 70 | 600 | 2.00 | 2.19 |
| 7 | 85% (2) PP + EAE + SEBS (3) 15% EPC (4) | 220 | terpolymer E + EA + AM (9) | 180 | DEHP | 50 | 500 | 2.97 | 3.04 |

TABLE 2

| | Outer layer Plasticized PCV composition | | | Intermediate layer | | Inner layer | | Resistance to delamination | |
|---|---|---|---|---|---|---|---|---|---|
| Ex. | Plasticizer | Proportion (1) | [μm] | Composition | [μ] | Composition | e [μm] | Before sterilization [N/mm] | After sterilization [N/mm] |
| 8 | DEHP | 50 | 350 | terpolymer E + EA + AM (9) | 280 | 85% (2) PP + EAE + SEBS (3) 15% EPC (4) | 400 | 1.26 | 3.25 |
| 9 | DEHP | 50 | 280 | terpolymer E + EA + AM (9) | 450 | 85% (2) PP + EAE + SEBS (3) 15% EPC (4) | 270 | 1.44 | 2.98 |

E=ethylene
EA=ethyl acrylate
PP=polypropylene
PVC=vinyl chloride polymer
MA=maleic anhydride
EAE=copolymer of ethylene and of an acrylic eater
EPC=copolymer of ethylene and of propylene
EBA=copolymer of ethylene and of butyl acrylate
EVA=copolymer of ethylene and of vinyl acetate
EMA=copolymer of ethylene and of methyl acrylate
SEBS=styrene-ethylene-butylene-styrene block copolymer
DEHP=di(2-ethylhexyl) phthalate 2. The multilayer tube according to claim 1, in which the modified copolymers are modified by grafting of maleic anhydride.

3. The multilayer tube according to claim 1, in which at least the inner layer or the outer layer comprises a polymeric material chosen from polypropylene, modified polypropylenes, polyethylene, modified polyethylenes, copolymers of ethylene and of propylene, modified copolymers of ethylene and of propylene, copolymers of ethylene and of vinyl acetate, modified copolymers of ethylene and of vinyl acetate, styrene-ethylene-butylene-styrene block copolymers, modified styrene-ethylene-butylene-styrene block copolymers, polyurethanes, modified polyurethanes, polyether amide block copolymers, vinyl chloride polymers, modified vinyl chloride polymers, plasticized vinyl chloride polymers, modified and plasticized vinyl chloride polymers, polyamides, copolymers of ethylene and of an acrylic ester, polyesters, copolyesters and mixtures thereof.

4. The multilayer tube according to claim 3, in which at least the inner layer or the outer layer comprises a polymeric material chosen from plasticized vinyl chloride polymers, polyurethanes, polyether amide block copolymers or mixtures of a copolymer of ethylene and of vinyl acetate with a copolyester.

5. The multilayer tube according to claim 3, in which at least the inner layer or the outer layer comprises a polymeric material chosen from polypropylene, copolymers of ethylene and of propylene, modified copolymers of ethylene and of propylene, ternary mixtures of polypropylene or of a copolymer of ethylene and of propylene or of a modified copolymer of ethylene and of propylene with a copolymer of ethylene and of an acrylic ester and with a styrene-ethylene-butylene-styrene block copolymer.

6. The multilayer tube according to claim 3, in which the inner layer comprises a polymeric material chosen from plasticized vinyl chloride polymers, polyurethanes, polyether amide block copolymers or mixtures of a copolymer of ethylene and of vinyl acetate with a copolyester, and the outer layer comprises a polymeric material chosen from polypropylene, copolymers of ethylene and of propylene, modified copolymers of ethylene and of propylene, ternary mixtures of polypropylene or of a copolymer of ethylene and of propylene or of a modified copolymer of ethylene and of propylene with a copolymer of ethylene and of an acrylic ester and with a styrene-ethylene-butylene-styrene block copolymer.

7. The multilayer tube according to claim 3, in which the inner layer comprises a polymeric material chosen from polypropylene, copolymers of ethylene and of propylene, modified copolymers of ethylene and of propylene, ternary mixtures of polypropylene or of a copolymer of ethylene and of propylene or of a modified copolymer of ethylene and of propylene with a copolymer of ethylene and of an acrylic ester and with a styrene-ethylene-butylene-styrene block copolymer, and the outer layer comprises a polymeric material chosen from plasticized vinyl chloride polymers, polyurethanes, polyether amide block copolymers or mixtures of a copolymer of ethylene and of vinyl acetate with a copolyester.

8. A method for the use in the medical field of the multilayer tube according to claim 1.

9. A multilayer sheet including layers as defined in the multilayer tube according to claim 1.

10. A method for the use in the medical field of the multilayer sheet according to claim 9.

11. A multilayer tube or sheet according to claim 1 which additionally has been subjected to an irradiation treatment using an electron beam and/or electromagnetic irradiation and/or including one or a number of usual crosslinking agents.

12. The multilayer tube according to claim 1, wherein said intermediate layer has a thickness from 15% to 30% of the total thickness of the tube wall.

13. The multilayer tube according to claim 1, having a resistance to delamination of at least 2.00N/mm.

14. The multilayer tube according to claim 1, having greater resistance to delamination after sterilization compared to before sterilization.

* * * * *